United States Patent [19]

Waletzky et al.

[11] Patent Number: 5,617,855
[45] Date of Patent: Apr. 8, 1997

[54] MEDICAL TESTING DEVICE AND ASSOCIATED METHOD

[76] Inventors: Jeremy P. Waletzky, 5039 Lowell St., Washington, D.C. 20016; Peter J. Wilk, 185 W. End Ave., New York, N.Y. 10023

[21] Appl. No.: 299,571

[22] Filed: Sep. 1, 1994

[51] Int. Cl.$^6$ ........................................................ A61B 5/00
[52] U.S. Cl. .......................... 128/653.1; 128/630; 395/2.6
[58] Field of Search ................................ 128/653.1, 630, 128/671; 351/209; 356/39; 364/413.02; 381/41–43; 382/118

[56] References Cited

U.S. PATENT DOCUMENTS

| | | |
|---|---|---|
| 4,783,802 | 11/1988 | Takebayashi et al. . |
| 4,894,777 | 1/1990 | Negishi et al. . |
| 4,975,960 | 12/1990 | Petajan . |
| 5,148,483 | 9/1992 | Silverman . |
| 5,412,738 | 5/1995 | Brunelli et al. . |
| 5,437,278 | 8/1995 | Wilk . |
| 5,507,291 | 4/1996 | Stirbl et al. . |
| 5,544,649 | 8/1996 | David et al. . |

*Primary Examiner*—Marvin M. Lateef
*Assistant Examiner*—Shawna J. Shaw
*Attorney, Agent, or Firm*—McAulay Fisher Nissen Goldberg & Kiel, LLP

[57] ABSTRACT

A medical testing device comprises an analog-to-digital converter for converting to an electrical digital signal a voice-frequency signal originating in a speech by a human speaker. The A/D converter is connected to a speech analyzing circuit which analyzes the digital signal to determine a value for a preselected first parameter characteristic of the speech, the parameter being taken from the group comprising frequency or tone, amplitude or loudness, and speed. A video camera or other component is provided for generating a video signal encoding an image of the human speaker's face during the speech. The camera is connected to an image analyzing circuit which processes the video signal to determine a value for a preselected second parameter characteristic of an emotional expression of the human speaker during the speech. A text encoder is provided for encoding a text corresponding in essential words to the speech. A correlation circuit is operatively connected to the speech analyzing circuit, the image analyzing circuit, and the text encoder for correlating values of the first parameter and the second parameter with words of the text.

26 Claims, 1 Drawing Sheet

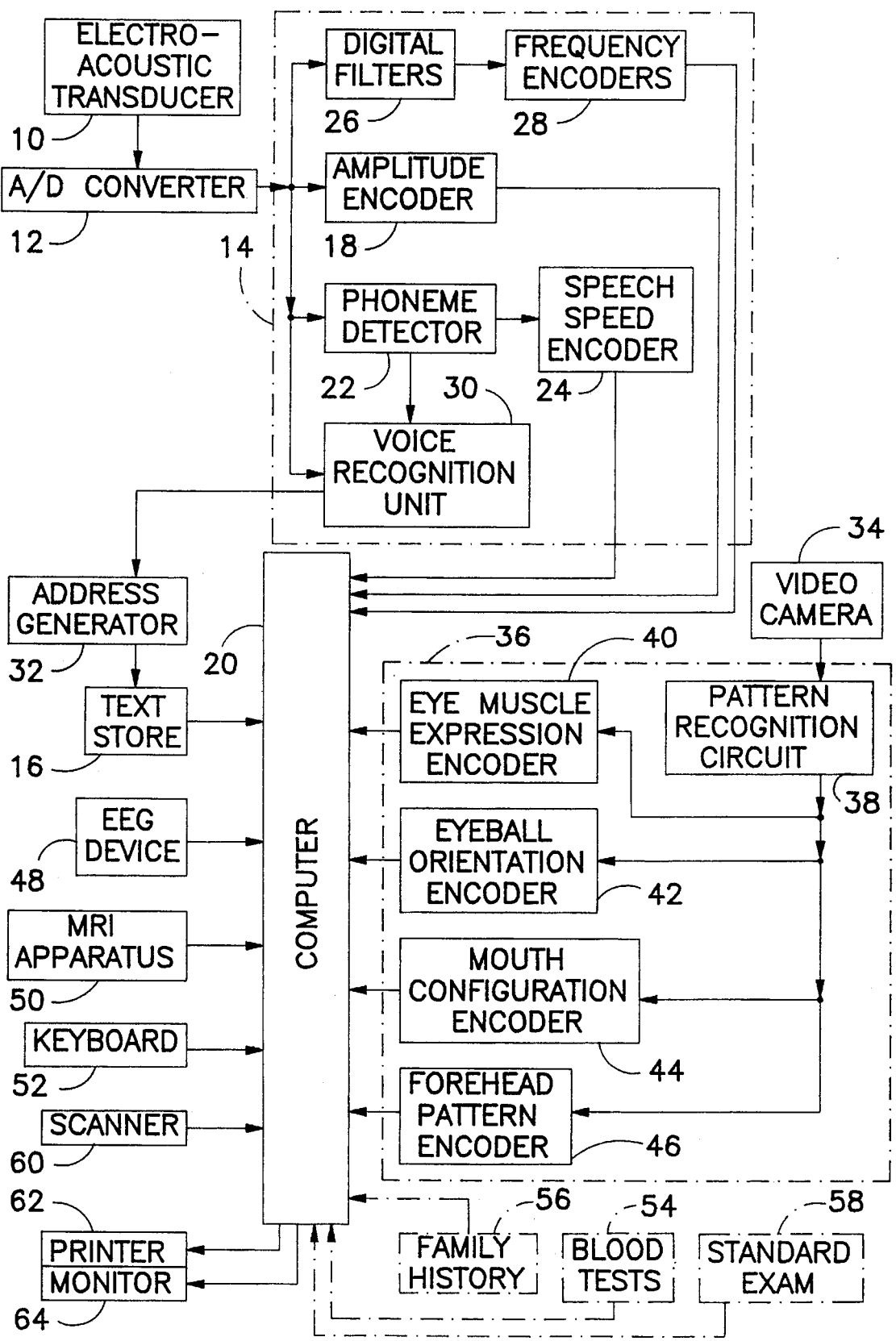

MEDICAL TESTING DEVICE AND ASSOCIATED METHOD

BACKGROUND OF THE INVENTION

This invention relates to a medical testing device and to an associated methodology.

One of the great difficulties in medicine is the proper diagnosis of human illnesses and abnormalities. This difficulty arises from the fact that proper diagnosis generally proceeds only from many years of experience. Because experience varies from practitioner to practitioner, a disease may frequently be accurately diagnosed only by a limited number of physicians who have had the requisite experience with the particular disease.

The difficulty of proper diagnosis is augmented in areas such as psychiatry and neurology where causes of illness are hidden and the symptoms themselves are many and varied.

Another problem with psychiatry and neurology, as many other disciplines of medicine, is that the experience required to make proper diagnoses and treatment also means that the physician is in a position to charge more for his or her services. In this era of political and societal concern over the costs of health care, a goal of advancing medical practice is to ensure adequate health care, including mental health care, for everybody, regardless of the ability of the individual to pay the health care costs. One goal in ensuring proper health care is to reduce the costs of that care.

OBJECTS OF THE INVENTION

An object of the present invention is to provide a method for furthering the advance of medicine to reduce costs while maintaining or upgrading the quality of care provided.

Another object of the present invention is to provide such a method which is of special use in areas of psychiatry and/or neurology.

Another, more particular, object of the present invention is to provide such a method which pools the experience of many physician practitioners in learning about the problems of any one individual patient.

A further particular object of the present invention is to provide a device for use in implementing the method of the invention.

These and other objects of the present invention will be apparent from the drawings and detailed descriptions herein.

SUMMARY OF THE INVENTION

A medical testing device comprises, in accordance with the present invention, an analog-to-digital converter for converting to an electrical digital signal a voice-frequency signal originating in a speech by a human speaker. The A/D converter is connected to a speech analyzing circuit which analyzes the digital signal to determine a value for a preselected first parameter characteristic of the speech, the parameter being taken from the group comprising frequency or tone, amplitude or loudness, and speed. A video camera or other component is provided for generating a video signal encoding an image of the human speaker's face during the speech. The camera is connected to an image analyzing circuit which processes the video signal to determine a value for a preselected second parameter characteristic of an emotional expression of the human speaker during the speech. A text encoder is provided for encoding a text corresponding in essential words to the speech. A correlation circuit is operatively connected to the speech analyzing circuit, the image analyzing circuit, and the text encoder for correlating values of the first parameter and the second parameter with words of the text.

A testing device in accordance with the present invention is primarily used, during an initialization or calibration phase, to collect data pertaining to the emotional responses of many patients to predetermined textual material. Of course, different texts may be used for characterizing the emotional responses of the same patients at different times. The testing device automatically monitors and measures vocal responses of the tested individual, as well as at least one facial parameter. Generally, it is contemplated that many parameters pertaining to the individual's facial expression are measured or derived, to characterize the individual's emotional state during the reading of the text.

According to another feature of the present invention, the speech analyzing circuit determines a value for frequency or tone of the speech, a value for amplitude or loudness of the speech, and a value for speed of the speech. The frequency parameter may be a plurality of values characterizing the timbre or tone of the individual's voice. Generally, all of these parameters, namely, spectral response, amplitude and speed of pronunciation, will vary from place to place throughout the previously composed or standardized text, depending on the content of the words, as well as on the reader's emotional predilections.

The image analyzing circuit analyzes the video signal to determine a value characterizing one or more predetermined facial muscles of the human speaker. For example, the muscles around the mouth can be characterized as having different kinds and degrees of tension, which are correlated with emotional states such as anger, determination, fear, despair, etc. Similar parametric characterizations may be made of the muscles about the eyes, the muscles of the forehead, etc.

Another characterizing parameter determinable through a simple pattern recognition program is movement of the eye. The extent, frequency, speed and direction of eye movements may all be detected and reduced to numerical values.

During the initialization or calibration phase, the reactions of the tested individual to the textual material are correlated with the material and with reactions of individuals of known emotional disorders. This correlation can be implemented using the combined knowledge experience of many practitioners. Once the initialization or calibration phase is completed, the testing device may be used in the automatic evaluation and diagnosis of individual patients, thus providing in one device the knowledge and experience of many expert psychiatrists and/or neurologists.

During the initialization or calibration phase, the device may also be used on people who might be characterized as psychologically normal or well adapted.

According to another feature of the present invention, the testing device further comprises means connected to the correlation circuit for providing electroencephalographic ("EEG") data regarding the human speaker to the correlation circuit. This EEG input may be provided continuously during the reading of text by the test subject. The EEG data is automatically analyzed, e.g., filtered, to determine spectral frequency response during a testing operation.

It is to be noted in this regard that the principal input to the correlation unit, i.e., the sampling of the vocal response and facial expression of the test subject, are provided periodically, at a rate sufficient to detect changes in emotional response of the tested individual due to the content of the textual material. Thus, at least four samples per second are recommended.

A medical testing method comprises, in accordance with the present invention, the steps of (a}) providing a preselected text to a human speaker, (b}) converting, to an electrical digital signal, a voice-frequency signal originating in a speech produced by the human speaker reading the text, (c}) automatically analyzing the digital signal to determine a value for a preselected first parameter characteristic of the speech, the parameter being taken from the group comprising frequency or tone, amplitude or loudness, and speed, (d}) generating a video signal encoding an image of the human speaker's face during the speech, (e}) automatically analyzing the video signal to determine a value for a preselected second parameter characteristic of an emotional expression of the human speaker during the speech, and (f}) automatically correlating determined values of the first parameter and the second parameter with words of the text.

Pursuant to another feature of the present invention, the automatic correlation includes the step of operating a computer to correlate determined values of the first parameter and the second parameter with words of the text.

In determining the speaker's emotional state by measuring the speaker's vocal response to the standardized, preselected text, the digital signal is analyzed to determine values for frequency or tone of the speech, amplitude or loudness of the speech and speed of the speech. As discussed above, a plurality of frequency values characterizing the timbre or tone of the individual's voice may be measured. In addition to spectral response, amplitude and speed of pronunciation are monitored and measured continually during the reading of the standardized text by the test subject.

As further discussed above, the video signal is analyzed to determine a value characterizing a predetermined facial muscle of the human speaker. Generally, it is contemplated that a plurality of facial muscles are automatically monitored, via a pattern recognition type computerized operation, to make a determination or characterization of emotional state. In addition, the video signal is analyzed to determine a value characterizing eye movement of the human speaker.

It is to be noted that in operating a computer to decipher facial expression and thus inferentially ascertain emotional state, all information available in a video signal should be taken into account. Such information includes color, texture, line, shape and any other automatically perceptible characteristics used in pattern recognition.

According to another feature of the present invention, the method also includes the step of providing electroencephalographic data regarding the human speaker and automatically correlating the electroencephalographic data with the determined values of the first (vocal) parameter and the second (visual) parameter and with words of the text. In addition, structural or morphological input may be entered into the correlating computer from an MRI apparatus or CAT scan. Generally, it is contemplated that this organic data is obtained at a time different from the reading of the textual material.

Other information provided to the correlating computer includes results of a mental status examination administered to the individual test subject (the "speaker"), results of a blood test administered to the test subject, family history data pertaining to the test subject, etc. In more advanced embodiments of the invention, other data automatically measured and reduced to parametric form for automatic correlation by computer may include odor molecules produced by the test subject during the test or at other times, and electromagnetic field measurements, e.g., so-called "auras."

A device and method in accordance with the present invention furthers the advance of medicine by providing steps for the automatization of complex psychiatric diagnosis. Automation will reduce costs while maintaining or upgrading the quality of care provided. The device and the method in accordance with the present invention serves to pool the knowledge and experience of many physician practitioners in learning about the problems of any one individual patient.

BRIEF DESCRIPTION OF THE DRAWINGS

FIG. 1 is a block diagram showing functional components of a medical testing device in accordance with the present invention.

DETAILED DESCRIPTION

As illustrated in FIG. 1, a medical testing device or system, particularly for use in investigating human emotional response with the eventual goal of automatic diagnosis of psychiatric or psychological disorders, comprises an acousto-electric transducer or microphone 10 connected at an output to an analog-to-digital converter 12. Converter or digitizer 12 functions to convert an analog output signal from transducer 10 to an electrical digital signal encoding a voice-frequency signal originating in a speech by a human speaker. Generally, it is contemplated that a human test subject will speak words of a pre-established standardized text, the words and content of which are stored in a text store 16.

A/D converter 12 is connected at an output to a speech analyzing circuit 14 which analyzes the digital signal to determine a value for a plurality of preselected parameters characteristic of the speech of the test subject. More particularly, speech analyzing circuit 14 includes a first encoder 18 for detecting the amplitude of the incoming signal and encoding the detected or measured amplitude in an output signal fed to a computer 20. This output signal essentially characterizes the instantaneous loudness of the person's speech.

Speech analyzing circuit 14 also includes a phoneme encoder 22 for detecting a sequence of phonemes or words and generating a rectangular wave signal which has a frequency proportional to the frequency of occurrence of phonemes in the speech spoken by the test subject. The rectangular wave is fed to an encoder 24 which transmits to computer 20 a signal encoding the speed of the speech.

Speech analyzing circuit 14 further includes a plurality of digital filters 26 and ganged frequency encoders 28 which provide to computer 20 an output signal characteristic of the tone or timbre of the test subject's speech. Frequency encoders 28 thus generate signals encoding the spectral composition of the test subject's speech.

Speech analyzing circuit 14 additionally includes a voice recognition circuit 30 for analyzing the incoming voice-frequency signal to determine a sequence of spoken words. The output of voice recogniton circuit 30 is fed to an address generator 32 which is in turn connected to text store 16 for reading out a sequence of pre-encoded content data from that unit to computer 20.

As further illustrated in FIG. 1, the medical testing device or system further comprises a video camera 34 or other component for generating a video signal encoding an image of the test subject's face during the speaking of the standardized textual material. Camera 34 is connected to an image analyzing unit 36 which processes the video signal to determine a value for a preselected parameter characteristic of an emotional expression of the human speaker during the speech. More particularly, camera 34 is connected to a pattern recognition circuit 38 of unit 36 which in turn is connected on an output side to a plurality of encoders 40, 42, 44, and 46 which provide computer 20 data as to facial expression of the individual test subject.

Encoder 40 generates a signal which encodes information about the configuration of the muscles about an eye of the test subject. This encoder thus provides computer 20 with information that the eye is closed, or squinting, or round and open. The inferences about the emotional state of the test subject to be drawn from that information is determined in part by information supplied by the other visual encoders 42, 44, and 46. A round eye may be indicative of fear, while a squinting eye is indicative of rage. A half open relaxed eye may indicate homeostasis.

Encoder 42 informs computer 20 of the orientation of an eyeball of the test subject. With input from encoder 42, computer 20 is able to track the movements of the eye, i.e., rolling, darting, shifting. These movements, and their periodicity, timing, speed, etc., are all expressive of conscious and subconscious emotional states of the test subject.

Encoder 44 signals computer 20 as to the orientaton and shape of the test subject mouth, while encoder 46 specifies the state of-the forehead and/or eyebrows of the test subject. Obviously, more encoders may be provided in image analyzing unit 26 for providing greater detail to computer 20.

Computer 20 is programmed to correlate the instantaneous input from speech analyzing circuit 14 and image analyzing circuit 36 with textual content as communicated to the computer by text store 16 in response to signals from voice recognition unit 30. During an initialization or calibration phase, computer 20 functions to collect data pertaining to the emotional responses of many test subjects to one or more texts. The testing device automatically monitors and numerically characterizes vocal responses and facial expressions of the test subjects. According to its programming, computer 20 correlates the responses of the test subject to the words of the text. Sometimes an individual's reaction to the text comes after its reading and sometimes beforehand, if the individual reads ahead before intoning the words.

Computer 20 is thus able to determine, from the input from speech analyzing circuit 14, whether the indivudal's voice is relaxed or stressed, smooth or unven. Similarly, from the facial expression information from image analyzing circuit 36, computer 20 is able to ascertain the existence of various states of concern, relaxation, irritation, etc.

As further shown in FIG. 1, the testing device further comprises an electroencephalographic ("EEG") apparatus 48 connected to the correlation forming computer 20 for providing electroencephalographic data regarding the individual test subject to the computer. This EEG input may be provided continuously during the reading of text by the test subject. The EEG data is automatically analyzed, e.g., filtered, by circuits internal to apparatus 48 to determine spectral frequency response during a testing operation.

Other input devices may be connected to computer 20 for supplementing the psychiatric, psychological and/or eurological information available to the computer. An MRI imaging apparatus 50 may be connected to computer 20 for providing three-dimensional structural data about the brain and spinal cord. A keyboard 52 is connected to computer 20 for enabling the manual input of data collected from other sources, for example, the results of blood tests 54, a family history 56, results of a standardized mental examination 58. Such information may alternatively be fed to computer 20 via a scanner 60.

In more advanced embodiments of the invention, other data is automatically measured and reduced to parametric form for automatic correlation by computer 20. For example, a molecular discriminator may be provided for differentiating between emotional states of a test subject on the basis of odor, i.e., molecular output of the individual. Another possible parametric indicator of a test subject's emotional states is electromagnetic field measurements, e.g., so-called "auras."

Computer 20 is provided with conventional output devices including a printer 62 and a monitor 64.

In a methodology implemented by the above-described apparatus, a preselected text is provided to a human test subject for reading thereby. The speech of the test subject is converted to an electrical digital signal and is then automatically analyzed to determine a value for a parameter characteristic of the speech. The parameter is taken from the group comprising frequency or tone, amplitude or loudness, and speed. In addition, the method also includes the step of generating a video signal encoding an image of the human speaker's face during the speech, automatically analyzing the video signal to determine a value for a preselected second parameter characteristic of an emotional expression of the human speaker during the speech, and automatically correlating determined values of the speech parameter(s) and the facial expression parameter(s) with words of the text.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A medical testing device comprising:

analog-to-digital conversion means for converting to an electrical digital signal a voice-frequency signal originating in a speech by a human speaker;

speech analyzing means operatively connected to said analog-to-digital conversion means for analyzing said digital signal to determine a value for a preselected first parameter of said speech indicative of an emotional state coexistent with said speech, said parameter being taken from the group comprising frequency or tone, amplitude or loudness, and speed;

video means for generating a video signal encoding an image of said human speaker's face during said speech;

image analyzing means operatively connected to said video means for analyzing said video signal to determine a value for a preselected second parameter characteristic of an emotional expression of said human speaker during said speech;

text encoding means for encoding a text corresponding substantially to said speech; and correlation means operatively connected to said speech analyzing means, said image analyzing means, and said text encoding means for correlating values of said first parameter and said second parameter with words of said text to characterize an emotional state of said human speaker partially induced by words of said text.

2. The device defined in claim 1 wherein said speech analyzing means includes:

first means for analyzing said digital signal to determine a value for frequency or tone of said speech;

second means for analyzing said digital signal to determine a value for amplitude or loudness of said speech; and third means for analyzing said digital signal to determine a value for speed of said speech.

3. The device defined in claim 1 wherein said image analyzing means includes means for analyzing said video signal to determine a value characterizing a predetermined facial muscle of the human speaker.

4. The device defined in claim 1 wherein said image analyzing means includes means for analyzing said video signal to determine a value characterizing eye movement of the human speaker.

5. The device defined in claim 1, further comprising means connected to said correlation means for providing electroencephalographic data regarding said human speaker to said correlation means.

6. A medical testing method comprising the steps of:

providing a preselected text to a human speaker;

converting, to an electrical digital signal, a voice-frequency signal originating in a speech produced by said human speaker reading said text;

automatically analyzing said digital signal to determine a value for a preselected first parameter of said speech indicative of an emotional state coexistent with said speech, said parameter being taken from the group comprising frequency or tone, amplitude or loudness, and speed;

generating a video signal encoding an image of said human speaker's face during said speech;

automatically analyzing said video signal to determine a value for a preselected second parameter characteristic of an emotional expression of said human speaker during said speech; and automatically correlating determined values of said first parameter and said second parameter with words of said text to characterize an emotional state of said human speaker induced by words of said text.

7. The method defined in claim 6 wherein said step of automatically correlating includes the step of operating a computer to correlate determined values of said first parameter and said second parameter with words of said text.

8. The method defined in claim 6 wherein said digital signal is analyzed to determine values for frequency or tone of said speech, amplitude or loudness of said speech, and speed of said speech.

9. The method defined in claim 6 wherein said video signal is analyzed to determine a value characterizing a predetermined facial muscle of the human speaker.

10. The method defined in claim 6 wherein said video signal is analyzed to determine a value characterizing eye movement of the human speaker.

11. The method defined in claim 6, further comprising the step of providing electroencephalographic data regarding said human speaker and automatically correlating said electroencephalographic data with the determined values of said first parameter and said second parameter and with words of said text.

12. The method defined in claim 6, further comprising the steps of administering a mental status examination to said human speaker and automatically correlating results of said mental status examination with said determined values.

13. The method defined in claim 6, further comprising the step of administering a blood test to said human speaker and automatically correlating results of said blood test with said determined values.

14. A medical testing device comprising:

analog-to-digital conversion means for converting to an electrical digital signal a voice-frequency signal originating in a speech by a human speaker;

speech analyzing means operatively connected to said analog-to-digital conversion means for analyzing said digital signal to determine a value for a preselected first parameter characteristic of said speech, said parameter being taken from the group comprising frequency or tone, amplitude or loudness, and speed;

video means for generating a video signal encoding an image of said human speaker's face during said speech;

image analyzing means operatively connected to said video means for analyzing said video signal to determine a value for a preselected second parameter characteristic of an emotional expression of said human speaker during said speech;

text encoding means for encoding a text corresponding substantially to said speech; and correlation means operatively connected to said speech analyzing means, said image analyzing means, and said text encoding means for correlating values of said first parameter and said second parameter with words of said text to provide a psychiatric or psychological diagnosis of said human speaker.

15. The device defined in claim 14 wherein said speech analyzing means includes:

first means for analyzing said digital signal to determine a value for frequency or tone of said speech;

second means for analyzing said digital signal to determine a value for amplitude or loudness of said speech; and third means for analyzing said digital signal to determine a value for speed of said speech.

16. The device defined in claim 14 wherein said image analyzing means includes means for analyzing said video signal to determine a value characterizing a predetermined facial muscle of the human speaker.

17. The device defined in claim 14 wherein said image analyzing means includes means for analyzing said video signal to determine a value characterizing eye movement of the human speaker.

18. The device defined in claim 14, further comprising means connected to said correlation means for providing electroencephalographic data regarding said human speaker to said correlation means.

19. A medical testing method comprising the steps of:

providing a preselected text to a human speaker;

converting, to an electrical digital signal, a voice-frequency signal originating in a speech produced by said human speaker reading said text;

automatically analyzing said digital signal to determine a value for a preselected first parameter characteristic of said speech, said parameter being taken from the group comprising frequency or tone, amplitude or loudness, and speed;

generating a video signal encoding an image of said human speaker's face during said speech;

automatically analyzing said video signal to determine a value for a preselected second parameter characteristic of an emotional expression of said human speaker during said speech; and automatically correlating determined values of said first parameter and said second parameter with words of said text to provide a psychiatric or psychological diagnosis of said human speaker.

20. The method defined in claim 19 wherein said step of automatically correlating includes the step of operating a computer to correlate determined values of said first parameter and said second parameter with words of said text.

21. The method defined in claim 19 wherein said digital signal is analyzed to determine values for frequency or tone of said speech, amplitude or loudness of said speech, and speed of said speech.

22. The method defined in claim 19 wherein said video signal is analyzed to determine a value characterizing a predetermined facial muscle of the human speaker.

23. The method defined in claim 19 wherein said video signal is analyzed to determine a value characterizing eye movement of the human speaker.

24. The method defined in claim 19, further comprising the step of providing electroencephalographic data regarding said human speaker and automatically correlating said electroencephalographic data with the determined values of said first parameter and said second parameter and with words of said text.

25. The method defined in claim 19, further comprising the steps of administering a mental status examination to said human speaker and automatically correlating results of said mental status examination with said determined values.

26. The method defined in claim 19, further comprising the step of administering a blood test to said human speaker and automatically correlating results of said blood test with said determined values.

* * * * *